United States Patent [19]

Hubbard et al.

[11] Patent Number: 4,688,572

[45] Date of Patent: Aug. 25, 1987

[54] MEDICAL/SPORTS THERMAL PACK

[75] Inventors: Vance M. Hubbard; Welton K. Brunson; Darrell S. Caldwell, all of Bedford, Tex.

[73] Assignee: Tecnol, Inc., Fort Worth, Tex.

[21] Appl. No.: 819,999

[22] Filed: Jan. 21, 1986

[51] Int. Cl.⁴ .................. A61F 7/08; A61F 7/10
[52] U.S. Cl. ..................... 128/402; 62/530; 126/204; 128/403; 383/901
[58] Field of Search ......... 128/156, 402, 403, 379, 128/380, 381, 382; 62/259.3, 530; 126/204; 383/901

[56] References Cited

U.S. PATENT DOCUMENTS

| | | | |
|---|---|---|---|
| 3,092,110 | 6/1963 | Duensing | 128/402 X |
| 3,409,008 | 11/1968 | Mortensen et al. | 128/156 |
| 3,491,761 | 1/1970 | Baker | 128/402 |
| 3,610,307 | 10/1971 | Huff et al. | 383/901 X |
| 4,204,543 | 5/1980 | Henderson | 128/403 X |
| 4,527,566 | 7/1985 | Abare | 128/402 |
| 4,585,003 | 4/1986 | Meistrell | 128/402 |

Primary Examiner—Anton O. Oechsle
Attorney, Agent, or Firm—Jerry W. Mills; Roger N. Chauza

[57] ABSTRACT

A thermal pack having a first pocket (12) and a second pocket (28) connected together by a stretchable material section (22), and therapeutic material holding bladders (14, 30) insertable into respective pockets. A pair of stretchable and Velcro-equipped straps (16, 18) attached to one pocket (28) are engagable with a brushed pile surface (20) of the other pocket (12). The pockets (12, 28) are constructed having a liner (34) for wicking to the outer surface moisture condensed on the bladders (14, 30), and constructed having a durable nonstretchable outer layer (32, 42).

20 Claims, 6 Drawing Figures

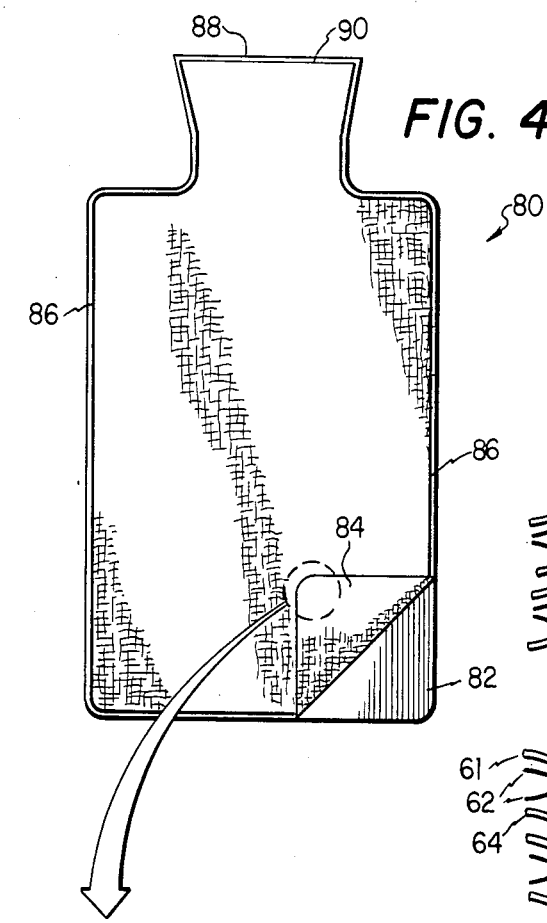
FIG. 4
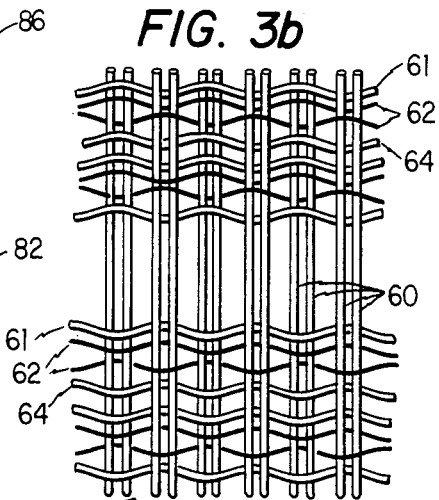
FIG. 3b
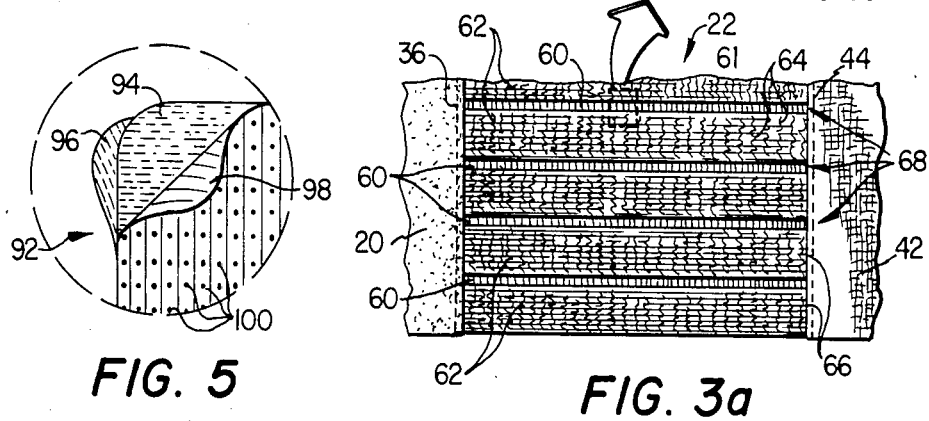
FIG. 5
FIG. 3a

MEDICAL/SPORTS THERMAL PACK

TECHNICAL FIELD OF THE INVENTION

The present invention relates generally to therapeutic limb treatment apparatus, and particularly to apparatus wrappable around a limb for the treatment of or the prevention of injury thereto.

BACKGROUND OF THE INVENTION

With the current popularity of health and fitness there is an increased emphasis on exercising by the normal person. In the sports and athletic field, exercising has always been essential. In the competitive professional area the care and treatment of athletes are becoming highly important. One area of concern which covers the private person, as well as the amateur and professional athlete is the protection of muscles from strain or cramping, or the treatment of muscles after an injury has occurred.

It is well known that for proper care and treatment, muscle tissues should be heated in certain circumstances and chilled in others. For example, before strenuous exercise, those muscles which tend to cramp should be heated to enrich the blood supply to the appropriate areas. On the other hand, sprained or strained muscle tissues should be chilled to reduce swelling and further damage. Before encountering strenuous exercise, it is not uncommon for persons to warm and limber muscles in a whirlpool of hot water. The problem with this approach is that more muscles are affected than need be, and the deadening effect of hot water tends to desensitize all the muscles immersed in the hot water.

Ice packs of various forms are well known in the medical art and are commonly applied to sprained or otherwise injured limbs. With knee injuries such as caused by hyperextension, or after knee surgery, the alternate application of hot and cold material to the joint is a regular practice. However, it has recently been recognized that since there is very little blood flow through the kneecap, or patella, the alternate hot and cold treatment thereto should be avoided. Most previously developed ice packs include a pouch for holding ice, and a strap, or pair of straps, for holding the pouch in contact with the muscles involved. While this approach may work with an immobilized person, such as a hospitalized patient, these ice packs re not well adapted for quickly changing from hot to cold treatments, nor for staying in place should the person move about or exercise. Moreover, such prior ice packs often provide undesirable temperature treatment to the patella while treating adjacent muscles.

Another problem common to many ice packs is the condensation that forms as a result of temperature gradient between the inside and outside of the container. Condensed moisture creates an undesirable situation in that the pack tends to slide on the wounded limb, bandages or tape cannot adhere either to the wet limb or pack, and the moisture tends to expand fabrics and loosen an otherwise firmly secured bandage or wrap. Any attempt to insulate the ice pack to reduce condensation only thwarts the transfer of coldness to the injured limb. Moisture impervious linings have also been suggested, such as alluded to in U.S. Pat. No. 4,527,566. However, suitable moisture resistant materials are generally characterized as being somewhat insulating, or become the mechanism for the formation of condensation thereon.

There is therefore a need for a multicompartmented thermal pack adapted for heating or chilling limb muscles, and adapted for staying in position while exercising with or without temparature treatment. There is also an associated need for a thermal pack which reduces the undesirable effects of condensed moisture, and which prevents undesirable temperature treatment of the patella when heating adjacent muscles.

SUMMARY OF THE INVENTION

The thermal pack according to the invention provides the capability for applying a cold pack or a hot pack, or both, to various limb muscles. In addition, the thermal pack includes an elastic section, and adjustable elastic Velcro-covered straps for maintaining the pack in position once applied to a limb. Moreover, when used around the joint of a limb, the elastic section conforms around an elbow or knee, for example, and further eliminates any relative movement of the pack with respect to the limb.

In the preferred embodiment of the invention, the thermal pack includes the first open-topped pocket and a second open-topped pocket joined by a unidirectional laterally expansible section. The first pocket has attached thereto, by elastic, a pair of fastening straps, each with Velcro-covered ends. The second pocket has an outer brushed pile surface covering for adjustable and removable engagement with the Velcro-covered straps. Each pocket is of a laminate fabric construction having durable outer coverings, and an inner moisture-wicking liner.

The foregoing structure itself can be applied to a limb solely for support purposes. In addition, there is provided a pair of waterproof bladders insertable into the liners of respective pockets. The bladders have sealable openings adapted for holding heated or cooled material.

In another embodiment of the invention, the bladders are integrally covered with a moisture-wicking fabric, whereby the corresponding pocket liners are eliminated and the construction thereof is simplified.

BRIEF DESCRIPTION OF THE DRAWINGS

Further features of the invention will be apparent from the following description of the invention when considered in conjunction with the drawings, in which:

FIG. 3a is an enlarged view of a portion of the unidirectional elastic section joining the pockets of the thermal pack;

FIG. 3b is an enlarged view of a portion of FIG. 3a, showing the fabric construction of the unidirectional panel;

FIG. 4 is an elevational view of the fabric-covered vinyl bladder, constructed according to an alternative embodiment of the invention; and FIG. 5 is an enlarged view of a portion of FIG. 5, illustrating the construction of the moisture-wicking pocket liner material.

DETAILED DESCRIPTION OF THE INVENTION

Figures 1, 2:
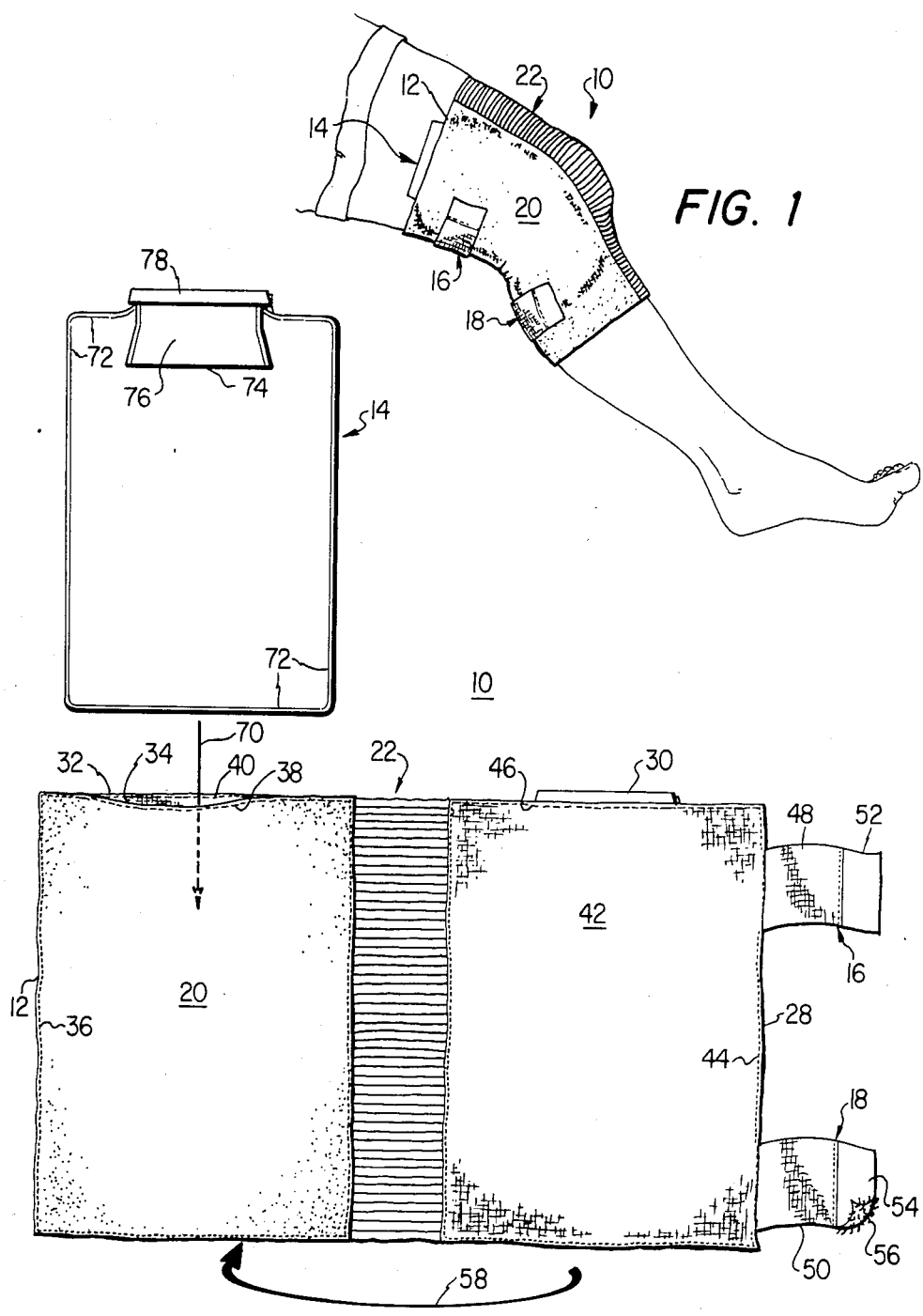
FIG. 1 is a side elevational view of the thermal pack according to the invention, as applied around the knee joint of a wearer.
FIG. 2 is an elevational view of the thermal pack, illustrating one bladder removed therefrom.

The application of the present invention is best understood by first referring to FIG. 1 of the drawings. The thermal ice pack, designated generally by 10, is well suited, but not limited to use round the jointed part of a person's limb, such as a knee or elbow. For illustrative purposes the thermal pack 10 is shown wrapped around the knee joint so that a hot or cold material, or both, can be applied to opposing sides of the joint.

The thermal pack 10 includes a pocket 12 in which a bladder 14 is insertable and held firmly wrapped around the limb by a pair of fasteners 16 and 18. The fasteners 16 and 18 are adjustably and removably engagable with an outside covering 20 of the pocket 12. A second pocket located on the other side of the knee, not shown in FIG. 1, is attached to the first pocket 12 by a unidirectional elastic section 22, which serves as a means for firmly wrapping the thermal pack 10 around the limb, yet allowing the knee complete freedom of movement. The elastic section 22 is stretchable in the direction of the lines. When worn on a limb as shown in FIG. 1, the elastic section 22 permits the wearer to move about without the thermal pack 10 working or sliding down the limb. In this manner, an athlete or hospital patient can move about freely without concern of the weight of the material in the bladders pulling the thermal pack 10 downwardly. In addition, the elastic section 22 prevents unnecessary temperature treatment of the patella while providing temperature treatment to the adjacent muscles.

In more detail, there is illustrted in FIG. 2 the details of the preferred embodiment constructed in accordance with the invention. The thermal pack 10 includes the open-topped first pocket 12, as noted above, and a second open-topped pocket 28 for holding a corresponding second bladder 30. The dimensions of each pocket 12 and 28 are about nine inches wide and twelve inches high. The first pocket 12 includes the outer fabric cover 20 peripherally sewn about three sides thereof to an inner fabric cover 32. The terms inner and outer as used herein connote the relative position of the pocket coverings when wrapped around a limb, the inner cover being adjacent the limb. The outer fabric cover 20 is constructed of a brushed-pile polyester material. The polyester material outer cover 20 allows air to move freely therethrough. The fabric inner cover 32 is constructed of a layer (not shown) of coarse woven durable polypropylene material. A coarse and loosely woven polypropylene material provides a desirable covering as it is strong, but yet allows the permeation of air or moisture therethrough.

A pocket liner 34, comprising a moisture-wicking polyester-rayon-polyester heat seal bonded laminate, is sewn between the inner and outer coverings 32 and 20. The synthetic laminate liner 34 is not a tight knit fabric, but is a thin layer heat seal bonded together at a matrix of locations covering a small percent of the surface area thereof. FIG. 5 illustrates the contruction of the liner material in more detail.

In outer cover 20 and inner cover 32 are stitched together around three corresponding edges thereof, as shown by dashed lines 36. The top edges of the moisture-wicking pocket liner 34 are sewn to the corresponding top edges of the outer cover 20 and inner cover 32, as shown by 38 and 40. The pocket 12 is thus open-topped for insertion thereinto of the bladder 14.

The bladder 14 is easily inserted or removed for replacement by other similar bags having fresh hot or cold material therein.

The second pocket 28 of the thermal pack 10 has identical inner (not shown) and outer 42 covers of coarse woven polypropylene material. As with pocket 12, pocket 28 includes between the inner and outer coverings 42 thereof a moisture-wicking pocket liner (not shown) with polyester-rayon-polyester fabric sides. The inner and outer covers 42 and the pocket liner of the second pocket 28 are peripherally attached at the sides and bottom by stitching 44. The corresponding top edges of the outer cover 42 and one side of the pocket liner are sewn by stitches 46. The upper edges of the inner cover and liner of pocket 28 are comparably sewn. The top of pocket 28 is thus open for insertion of the second bladder 30 into the liner, as shown.

Also stitched to the second pocket 28 are fastening straps 16 and 18. Each fastening strap 16 and 18 includes an elastic part 48 and 50, as well as Velcro hook material 52 and 54 stitched to the ends thereof. The conventionally available unidirectionally stretchable elastic material. The elastic parts 48 and 50 stretch outwardly away from the pocket edge to which the parts 48 and 50 are attached. The Velcro material 52 and 54, having the hook-like elements 56, is sewn to the elastic parts 48 and 50, as shown in FIG. 2. With this construction, when the thermal pack 10 is wrapped around a limb, as indicated by arrow 58, the hooks 56 are engagable at any location on the brushed-pile outer covering 20 of the first pocket 12.

It should thus be appreciated that the thermal pack 10 is adapted to fit around any size limb by appropriately engaging the hooks 56 of the separate Velcro ends 52 and 54 at desired lateral locations on the brushed pile surface of the first pocket outer cover 20. This is highly desirable if extensive limb swelling is encountered, as the individual fastening straps 16 and 18 can be independently and continually readjusted to maintain firm contact of the pack 10 with the limb, and yet allow circulation of blood through the limb. Indeed, one or both the straps can be adjusted, or can be placed in engagement on the pile surface 20 in a skewed or obliquely oriented manner. For large limbs, or excessively swollen limbs, the Velcro mterial ends 52 and 54 can be engaged near the outside edge of the brushed-pile covering 20. In this manner there are no exposed Velcro hook elements in contact with the wearer's skin to cause irritation, as would be if the entire surface of the fastening straps 16 and 18 were covered with the Velcro hook material.

The placement and adjustment of the pockets 12 and 28 about a limb is further facilitated by the elastic section 22 which can be stretched to accommodate various sized limbs. In the preferred form of the invention, the first pocket 12 is spaced apart from the second pocket 28 and connected by a two inch wide unidirectionally stretchable elastic section 22. The elastic section 22 accommodates any limb protrusion, such as a wound or another bandage, or a joint, and thus permits conformance of the thermal pack 10 thereto. The ability of thermal pack 10 to conform to the shape of a limb also reduces the possibility of the pack slipping on the limb. This is highly important as the bladders 14 and 30 can hold a total of about six pounds of crushed ice.

In accordance with the preferred form of the invention, the elastic section 22 includes a plurality of monofilament nylon strands to prevent stretching in a direction coaxial with the limb. The unidirectional stretchable elastic is best illustrated in FIGS. 3a and 3b. The monofilament nylon strands 60 comprise nylon 148 denier 5.5 mil. Covering the strands 60, and woven in the direction of the lines representing the section 22 in FIGS. 1 and 2, are various filler and foundation synthetic yarns, and elastic materials. An elastic material 61 is woven with the nylon monofilament strands 60. The elastic material is a composite structure including a polyester spandex 377 denier material, and a textured nylon type 6,6 70/34. Woven to provide body to the elastic section 22 are warp yarn textured nylon threads, type 6,6 2/100/34, designated by reference character 62. A third fabric strand 64 is woven together with strands 61 and 62, and is identified as a warp yarn textured nylon, type 6,6 2/70/34. Strand 64 operates to lock the nylon filament strands 60 in place. The pattern of these strands are repeated. Unidirectional material of the type described can be obtained from the George C. Moore Corp., P. O. Box 1634, Providence, R.I. 02903. The elastic material 61, the warp yarn 62 and support strands 64 are woven around the nylon strands 60 in lateral panels 66 about one fourth inch wide. The nylon strands 60 are not densely packed and are exposed at areas 68. Thus, the tissue of the limb thereunder can be visually examined through the stretched material without removing the thermal pack 10. In addition, the nylon strands 60 prevent the elastic section 22 from narrowing when stretched in a direction transverse to the strands 60.

The bladders 14 and 30 are identically constructed of a heavy gauge plastic, such as ten mil guage polyvinylchloride. Both bladders are insertable into their respective pockets, as shown by arrow 70 in FIG. 2. The bladder 14 is formed of two flat sheets of vinyl, heat sealed 72 along the outer peripheral edges thereof, except at the mouth 74. The bladder 14 includes a neck 76 and the open mouth 74 through which the bladder 14 may be filled with hot or cold water, ice or other thermal material. The bladder neck 76 is sealed off by a clamp 78 which pinches the neck 76 to provide a waterproof compartment within the bladder 14. The seal arrangement is more thoroughly described in U.S. Pat. No. 4,347,848, the disclosure of which is incorporated herein. Of course, other types of bladders and sealing arrangements may be employed in connection with the thermal pack 10.

In FIGS. 4 and 5 there is illustrated another embodiment of a bladder 80 adapted for use with thermal pack 10 of the invention. Bladder 80 is constructed with the same polyvinylchloride water-proof material 82 as bladder 14 shown in FIG. 2. In addition, bladder 80 has an external fabric covering 84 comprising a moisture-wicking material, such as a layered polyester-rayon-polyester composition. The external fabric covering 84 is shown, for reasons of clarity, pulled back from the vinyl 82. The vinyl 82, together with the external fabric covering 84, is heat sealed 86 along the peripheral edges thereof to form an integral construction. Of course, the vinyl layers are not heat sealed together at the mouth 88 of the bladder, but each layer of the liner fabric 84 is heat sealed 90 to the adjacent vinyl layer thereat.

The composition of synthetic materials comprising the liners 34 (of FIG. 2) and 84 is not moisture absorbent, but rather exhibits a "wicking" characteristic by carrying condensed moisture away from the bladder 14. Moisture which condenses on the bladder vinyl 82 is thus carried to the outer coverings of pack 10 where it is evaporated. This is advantageous, as any water formed from ice which may have inadvertently fallen between the liner 84 and the vinyl 82 is transferred to the outside of the pack 10 where it is eventually evaporated. With this construction, the moisture is not trapped within the pack 10.

Further shown in FIG. 5 is an enlarged and delaminated section of the moisture-wicking liner material 92. A rayon fiber layer 94 is sandwiched between polyester layers 96 and 98. All three layers are bonded together by a matrix of heat seal bonds, shown by 100.

It should be understood that when the bladder 80 is used in connection with the thermal pack 10 shown in FIG. 2, the moisture-wicking pocket liners can be eliminated.

From the foregoing, it should be appreciated that the thermal pack can be equipped with hot or cold material within the bladder for appropriate treatments of limb muscles. The thermal pack is wrapped around the limb in such a fashion that the pockets contact the desired muscles to be treated. A moisture-wicking fabric is provided for isolating the wearer from condensation which may form on the bladders. Moreover, the bladders are removable from the pockets, whereby the thermal pack can be used as a support. In addition, the thermal pack is constructed so that it is adjustable about limbs of various sizes, and adapted for application around a limb joint. To that end, the thermal pack includes a unidirectional elastic section which readily conforms to limb curvature, and which prevents the pack from inadvertently sliding along the limb.

The preferred embodiments of the invention have been described above in detail. However, various modifications and additions to the thermal pack are undoubtedly possible by those skilled in the art without departing from the spirit and scope of the invention as claimed hereinbelow.

What is claimed is:

1. A thermal pack, comprising:
    plural compartments each constructed of an inner and outer nonstretchable material to form a pocket;
    a pocket liner formed of a moisture-wicking material and disposed within each said pocket for holding a therapeutic material against the body part of a user;
    a pressure responsive fastening material disposed on a side surface of one said compartment;
    elastic means disposed between and integrally connecting said compartments together for allowing said pack to expand in a direction for conforming around different body shapes; and
    plural individual elastic fastening straps attached to another said compartment and engageable to said fastening material on said side surface of said one compartment for holding said pack wrapped around the body part of said user 2. The thermal pack of claim 1 wherein said elastic means is stretchable in only a single direction.

3. The thermal pack of claim 1 wherein each said fastening strap includes pressure responsive fastening material engageable with said fastening material on the side surface of said one compartment.

4. The thermal pack of claim 1 wherein each said compartment is open topped and includes a bladder containing said therapeutic material.

5. The thermal pack of claim 4 wherein each said bladder is removable from a respective said compartment.

6. The thermal pack of claim 1 wherein said liner material comprises polyester and rayon.

7. The thermal pack of claim 1 wherein said pressure responsive fastening material on the side surface of said one compartment is in the form of an outer cover comprising a brushed pile material.

8. The thermal pack of claim 7 wherein said fastening straps comprise expandable straps with hook-like elements engagable with the outer cover of said one compartment.

9. The thermal pack of claim 8 wherein the hook-like elements are disposed only on the ends of said straps.

10. A thermal pack wrappable around a limb, comprising:
a first open-topped pocket having a nonstretchable material defining an inside surface, a pile material defining an outside surface, said inside and outside surface being fastened together along three peripheral edges thereof;
a second open-topped pocket having a nonstretchable material defining an inside surface being fastened together along three peripheral edges thereof;
a pocket liner formed of a moisture-wicking and air permeable material disposed within each pocket;
stretchable elastic means disposed between said pockets for connecting side edges of said first and second pockets together;
first and second bladders for holding thermal material and sized for insertion into respective ones of said pockets, and
a plurality of stretchable straps connected proximate a side edge of said second pocket, each strap including pressure responsive attachment means attached to the terminal end thereof for removable engagement with said pile material of said first pocket.

11. The thermal pack of claim 10 wherein said stretchable elastic means extends along the entire side edge of each said pocket.

12. The thermal pack of claim 11 wherein said stretchable elastic means is stretchable in only a single direction transverse to said side edges.

13. The thermal pack of claim 12 wherein said stretchable elastic comprises a plurality of substantially parallel nylon filaments, and interwoven therewith and substantially transverse thereto a plurality of (a) strands comprising polyester spandex and textured nylon, (b) strands comprising warp yard textured nylon and (c) strands comprising filling yarn monofil nlylon.

14. A thermal bladder for use in ice packs, comprising:
a water proof container for containing thermal material; and
a moisture-wicking material covering said container and made integral thereto by a matrix of individual bonds over the surface thereof.

15. The bladder of claim 14 further including a seal extending substantially peripherally about said integral container and material for sealing said container and for making said material integral therewith.

16. The bladder of claim 14 wherein said moisture-wicking material comprises polyester-rayon-polyester layers heat seal bonded in said matrix.

17. A thermal pack, comprising:
a plurality of bladders, each said bladder having a moisture-wicking material integral therewith;
plural open-topped compartments, each for holding one said bladder and each said bladder adapted for holding a therapeutic material adjacent the body part of a user;
a pressure responsive fastening material disposed on a side surface of one said compartment;
elastic means disposed between and integrally connecting said compartments together for allowing said pack to expand in a direction for conforming around different body shapes; and
plural individual elastic fastening straps attached to the other said compartment and engageable to the fastening material on said side surface of said one compartment for holding said pack wrapped around the body part of the user.

18. The thermal pack of claim 17 wherein moisture-wicking material is heat bonded to said bladders.

19. A thermal pack wrappable around a limb, comprising:
first and second open-topped pockets;
stretchable elastic means disposed between said pockets and connecting one side edge of each said first and second pockets together;
first and second bladders for holding thermal material and sized for insertion into respective ones of said pockets;
pile material covering the outer surface of said first pocket;
a plurality of stretchable straps connected to a side edge of said second pocket, each strap including pressure responsive attachment means attached to the terminal end thereof for removable engagement with said pile material of said first pocket; and
a moisture-wicking material having a matrix of heat seal bonding points over the surface thereof and being integral with and lining the inside of each said pocket.

20. The thermal pack of claim 19 wherein said moisture-wicking material comprises polyester-rayon-polester layers bonded together.

* * * * *

UNITED STATES PATENT AND TRADEMARK OFFICE
CERTIFICATE OF CORRECTION

PATENT NO.   : 4,688,572
DATED        : August 25, 1987
INVENTOR(S)  : Vance M. Hubbard, et al.

It is certified that error appears in the above-identified patent and that said Letters Patent is hereby corrected as shown below:

Col. 7, line 21, after "inside surface" insert --and an outside surface, said inside and outside surface-- line 49, "nlylon" should be --nylon--.

Signed and Sealed this

Nineteenth Day of January, 1988

Attest:

DONALD J. QUIGG

Attesting Officer

Commissioner of Patents and Trademarks